(12) United States Patent
Rehfeld et al.

(10) Patent No.: US 9,733,173 B2
(45) Date of Patent: Aug. 15, 2017

(54) METHOD FOR SELECTING AN INTERLAYER FOR VIBROACOUSTIC DAMPING, INTERLAYER AND GLAZING UNIT COMPRISING SUCH AN INTERLAYER

(71) Applicant: Saint-Gobain Glass France, Courbevoie (FR)

(72) Inventors: Marc Rehfeld, Ezanville (FR); David Fournier, Breteuil (FR)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 244 days.

(21) Appl. No.: 14/747,352

(22) Filed: Jun. 23, 2015

(65) Prior Publication Data

US 2015/0283959 A1 Oct. 8, 2015

Related U.S. Application Data

(62) Division of application No. 12/906,747, filed on Oct. 18, 2010, now Pat. No. 9,102,122.

(30) Foreign Application Priority Data

Aug. 24, 2010 (FR) .................................. 10 56725

(51) Int. Cl.
*G01N 3/24* (2006.01)
*G01N 3/22* (2006.01)
(Continued)

(52) U.S. Cl.
CPC ................. *G01N 3/22* (2013.01); *B32B 7/02* (2013.01); *B32B 17/10* (2013.01);
(Continued)

(58) Field of Classification Search
CPC ........ G01N 3/22; B60R 13/0815; B32B 7/02; B32B 17/10; B32B 17/10036; B32B 17/10761
(Continued)

(56) References Cited

U.S. PATENT DOCUMENTS 3,592,726 A 7/1971 Blizard
5,190,826 A * 3/1993 Asahina ............ B32B 17/10009
181/176
(Continued)

FOREIGN PATENT DOCUMENTS

JP 2001-206742 7/2001

OTHER PUBLICATIONS

Cadogan et al., "Plasticizers," Ullmann's Encyclopedia of Industry Chemistry, pp. 599-618, (2000).

*Primary Examiner* — Benjamin Schmitt
(74) *Attorney, Agent, or Firm* — Oblon, McClelland, Maier & Neustadt, L.L.P.

(57) ABSTRACT

The invention relates to a method for selecting a viscoelastic plastic interlayer including two outer layers and a central layer that can be incorporated between two glass sheets of a glazing unit, the method includes providing first and second components that constitute respectively the central layer and the outer layers, measuring the shear modulus G' of the first and second components, selecting the material of the second component only if $G' \geq 3 \times 10^7$ Pa at 20° C. and between 100 Hz and 240 Hz, and setting the thickness h of the first component so that h is between 0.31 mm and 1.20 mm and so that $g = G'/h$ is between $5.58 \times 10^8$ Pa/m and $2.37 \times 10^9$ Pa/m at 20° C. and between 100 Hz and 240 Hz.

4 Claims, 4 Drawing Sheets

(51) Int. Cl.
*B60R 13/08* (2006.01)
*B60J 1/00* (2006.01)
*E06B 3/67* (2006.01)
*B32B 7/02* (2006.01)
*B32B 17/10* (2006.01)
*B60J 1/20* (2006.01)
*G01N 19/04* (2006.01)

(52) U.S. Cl.
CPC .. *B32B 17/10036* (2013.01); *B32B 17/10761* (2013.01); *B60J 1/001* (2013.01); *B60J 1/2097* (2013.01); *B60R 13/08* (2013.01); *B60R 13/0815* (2013.01); *E06B 3/67* (2013.01); *E06B 3/6707* (2013.01); *G01N 19/04* (2013.01); *Y10T 428/2495* (2015.01); *Y10T 428/24942* (2015.01); *Y10T 428/24967* (2015.01)

(58) Field of Classification Search
USPC .......................................... 73/788, 789, 841
See application file for complete search history.

(56) References Cited

U.S. PATENT DOCUMENTS

| | | | |
|---|---|---|---|
| 5,227,241 A * | 7/1993 | Chaussade | B32B 17/10036 428/212 |
| 7,829,192 B2 | 11/2010 | Boure et al. | |
| 2002/0006504 A1* | 1/2002 | Rehfeld | B32B 17/10036 428/212 |
| 2005/0077826 A1* | 4/2005 | Watanabe | B32B 7/02 313/587 |
| 2006/0070694 A1 | 4/2006 | Rehfeld et al. | |
| 2010/0295331 A1 | 11/2010 | Rehfeld et al. | |
| 2013/0316158 A1 | 11/2013 | Rehfeld et al. | |

* cited by examiner

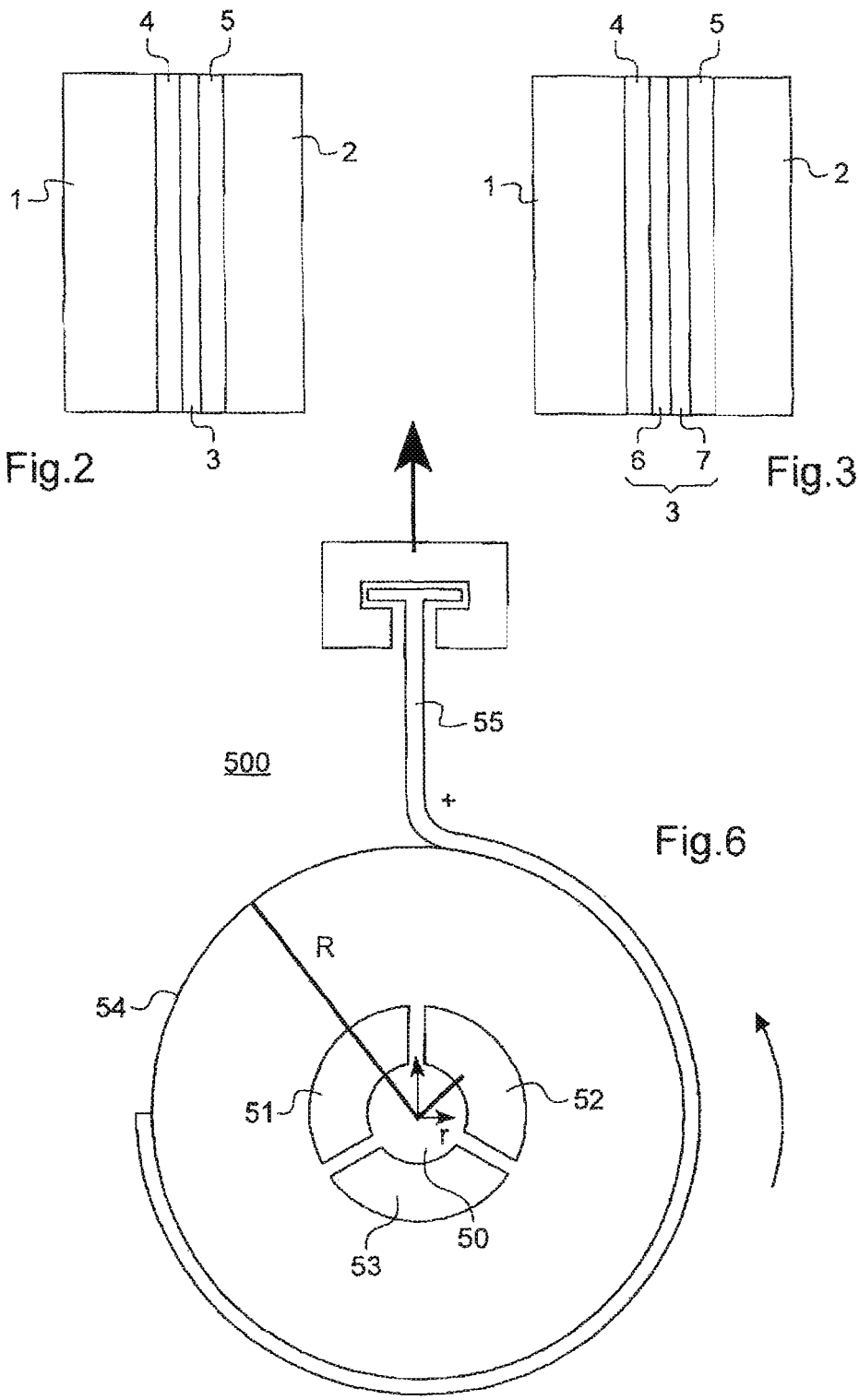

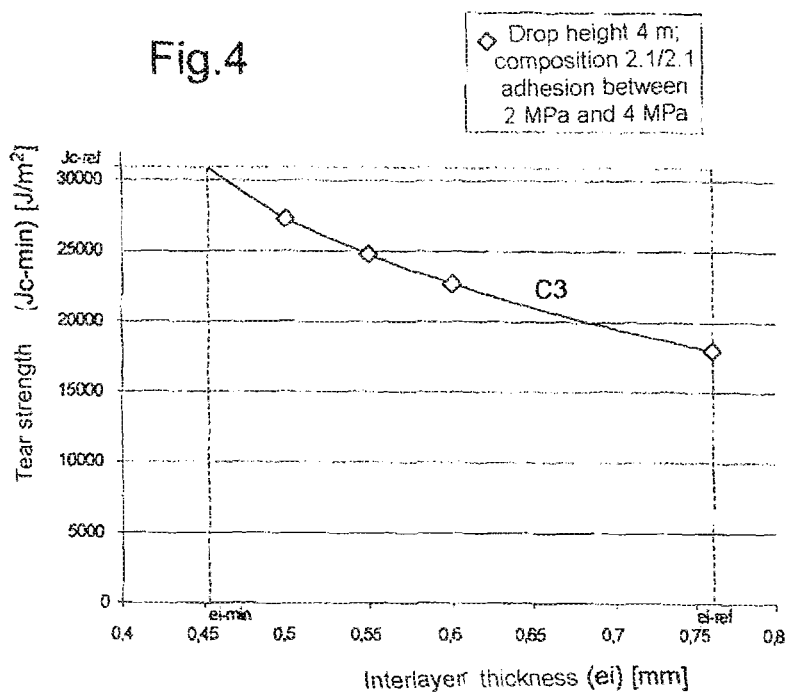
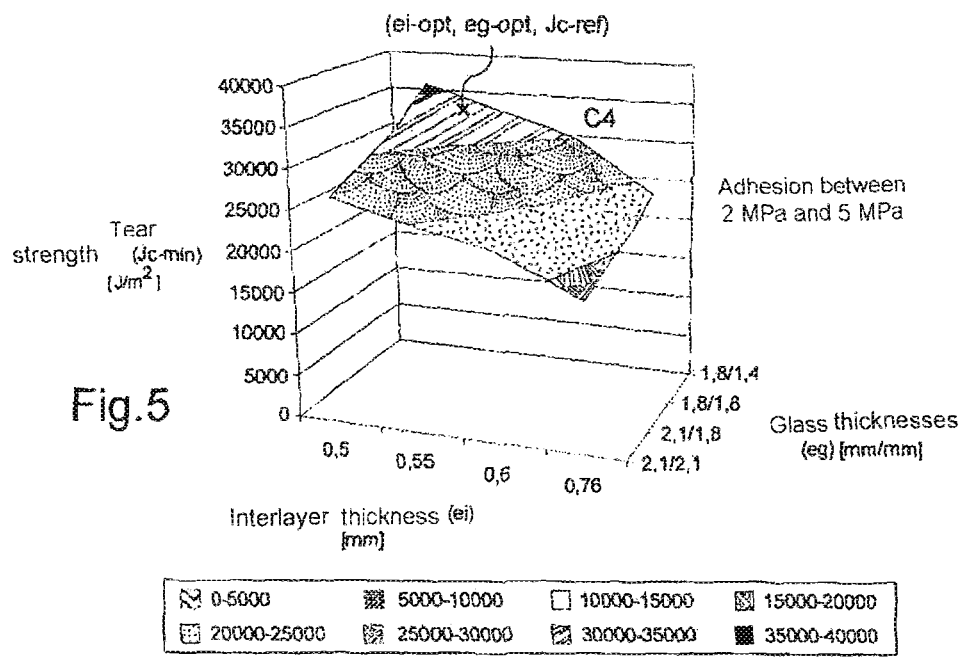

METHOD FOR SELECTING AN INTERLAYER FOR VIBROACOUSTIC DAMPING, INTERLAYER AND GLAZING UNIT COMPRISING SUCH AN INTERLAYER

CROSS-REFERENCE TO RELATED APPLICATION

This application is a division of U.S. application Ser. No. 12/906,747 filed Oct. 18, 2010, which claims priority under 35 U.S.C. §119 from prior French Application No. 10 56725 filed Aug. 24, 2010, the entire contents of each of which are incorporated herein by reference.

BACKGROUND OF THE INVENTION

Field of the Invention

The invention relates to a method for selecting an interlayer having an acoustic damping property in order to be incorporated into a laminated glazing unit, intended in particular for vehicles of locomotion, in particular a motor vehicle.

Discussion of Background

Among all the qualities contributing to comfort in modern means of transport such as trains and motor vehicles, silence has become the determining factor.

Acoustic comfort has been improved now over several years, by dealing with noise, such as noise from the engine, tires or suspension, and this at their source or during their propagation through the air or solids, by means for example of absorbent coatings or elastomeric connecting components.

The shapes of vehicles have also been modified in order to improve penetration through the air and to reduce turbulence that is itself a source of noise.

For several years, emphasis has been given to the role that glazing units can play in improving acoustic comfort, in particular laminated glazing units comprising plastic interlayer films. Laminated glazing units have, in addition, other advantages such as eliminating the risk of flying fragments in the case of sudden breakage, and impeding break-ins.

It has been demonstrated that the use of standard plastic films in laminated glazing units is not suitable for improving acoustic comfort. Specific plastic films have thus been developed that have damping properties enabling acoustic comfort to be improved.

In the following description, reference to a damping film relates to a viscoelastic plastic film that provides improved damping of vibrations in order to give the glazing unit a function of noise reduction.

It has been shown that the acoustic performance of a glazing unit depends on the value of the loss factor tan $\delta$ of the material constituting the interlayer film. The loss factor is the ratio between the energy dissipated in the form of heat and the elastic strain energy; it characterizes the capacity of the material to dissipate energy. The higher the loss factor, the greater the energy dissipated and therefore the more the material plays its damping role.

This loss factor varies as a function of the temperature and of the frequency. For a given frequency, the loss factor reaches its maximum value at a temperature known as the glass transition temperature.

The materials used as interlayers of laminated glazing units are viscoelastic plastic films, of acrylic polymer or acetal resin or else polyurethane type for example, which have quite a high loss factor, such as at least greater than 0.6 for a given temperature range and for a given frequency range.

The loss factor tan $\delta$ is assessed using a viscoanalyzer. The viscoanalyzer is a machine that makes it possible to subject a specimen of material to strains under precise temperature and frequency conditions, and thus to obtain and process all of the rheological magnitudes that characterize the material.

It has also been described, regarding the integration of a damping interlayer in a laminated glazing unit, that the loss factor tan $\delta$ should not be considered alone but that the shear modulus G' constitutes another characteristic to be taken into account in the damping property of the interlayer. Document EP-A-844 075 teaches that, in order to damp vibrations, the interlayer of the laminated glazing unit must correspond to particular values as regards the shear modulus G' and the loss factor tan $\delta$. It is recalled that the shear modulus G' characterizes the stiffness of the material; the higher G', the stiffer the material, and the lower G', the more flexible the material. The shear modulus depends on the temperature and on the frequency. The shear modulus G' is also assessed using a viscoanalyzer. This document describes that the loss factor tan $\delta$ of the interlayer is greater than 0.6 and the shear modulus G' of the interlayer is less than $2 \times 10^7$ Pa for temperatures between 10° C. and 60° C. and frequencies between 50 Hz and 10 000 Hz, in order to damp, more particularly, noises of solid-borne origin.

Furthermore, when the laminated glazing unit is used as a windshield, it is subjected to acoustic vibrations that are specific to it. Thus, the four first natural frequencies of the windshield, and in particular the second and third natural frequencies of the windshield, between 100 Hz and 240 Hz, are particularly annoying, acoustically speaking. The interlayer of document EP-A-844 075 is suitable for damping solid-borne noises, but not for the vibroacoustic damping of the first natural frequencies of the windshield, in particular the second and third natural frequencies.

There is therefore a need for a method for selecting an interlayer which makes it possible to optimize the damping of the first natural frequencies of a windshield, in particular of the second and third natural frequencies of the windshield, without weighing down the windshield.

SUMMARY OF THE INVENTION

For this, the invention proposes a method for selecting a viscoelastic plastic interlayer comprising two outer layers and a central layer and intended to be incorporated between two sheets of glass of a glazing unit, the method comprising the following steps:

a first component made of a viscoelastic plastic material intended to constitute the central layer and a second component made of a viscoelastic plastic material intended to constitute the outer layers are provided, the shear modulus G' of the first component and of the second component are measured by means of a viscoanalyzer, the material of the second component is selected only if its shear modulus G' is greater than or equal to $3 \times 10^7$ Pa at 20° C. and for a range of frequencies between 100 Hz and 240 Hz, the thickness h of the first component is fixed so that h lies between 0.31 mm and 1.20 mm and so that the shear parameter g=G'/h, G' being the shear modulus, is between $5.58 \times 10^8$ Pa/m and $2.37 \times 10^9$ Pa/m at 20° C., and for a frequency range between 100 Hz and 240 Hz.

According to another feature, the thickness h of the first component is set so that h is between 0.50 and 0.90 mm and so that G'/h is between $7.56 \times 10^8$ Pa/m and $1.42 \times 10^9$ Pa/m at 20° C. and for a frequency range between 100 Hz and 240 Hz.

According to another feature, the method comprises, in addition, before the step of setting the thickness h, the following steps:
- the loss factor tan δ of the first component is measured by means of the viscoanalyzer; and
- the first component is selected only if its loss factor tan δ is greater than 0.6.

According to another feature, the method comprises, in addition, the following step:
- the material of the second component is selected only if its shear modulus G' is between $10^8$ Pa and $2 \times 10^8$ Pa at 20° C. and for a frequency range between 100 Hz and 240 Hz.

According to another feature, the method comprises, in addition, the following steps:
- it is verified that the adhesion of the material of the second component is compatible with the requirements of Regulation R43 by twisting a specimen of the interlayer constituted of the material of the second component bonded to two glass sheets, by measuring the torsional force at which separation of the interlayer constituted of the material of the second component with the glass sheets is initiated, and by calculating from this force the corresponding adhesive shear strength, and this value of the adhesive strength is compared with a range of admissible values so that any laminated glazing unit withstands the stresses corresponding to Regulation R43; and
- the thickness e of the second component is set in the following manner:
  - a reference laminated glazing unit is identified that withstands the stresses corresponding to Regulation R43 and which comprises two sheets of glass and an interlayer constituted of the material of the second component;
  - the tear strength of the interlayer of the reference laminated glazing unit, the thickness of the interlayer of the reference laminated glazing unit and the thickness of the glass sheets of the reference laminated glazing unit are determined;
  - using a graph representative of the minimum interlayer tear strength required so that any laminated glazing unit withstands the stresses corresponding to Regulation R43, as a function of the interlayer thickness of any laminated glazing unit, this graph being established for a substrate thickness of any laminated glazing unit equal to the substrate thickness in the reference laminated glazing unit, the minimum required interlayer thickness is deduced which corresponds to a minimum required interlayer tear strength value equal to the tear strength of the interlayer of the reference laminated glazing unit; and
  - the thickness e of the second component is set so that e is greater than or equal to said optimum interlayer thickness value.

There is also a need for an interlayer which makes it possible to optimize the damping of the first natural frequencies of a windshield, in particular of the second and third natural frequencies of the windshield, without weighing down the windshield.

For this, the invention proposes a viscoelastic plastic interlayer intended to be incorporated between two glass sheets of a glazing unit in order to give it vibroacoustic damping properties, the interlayer comprising:
- two outer layers made of a viscoelastic plastic material, the shear modulus G' of which is greater than or equal to $3 \times 10^7$ Pa at 20° C. and for a frequency range between 100 Hz and 240 Hz,
- a central layer having vibroacoustic damping properties, of thickness h, so that h is between 0.31 mm and 1.20 mm and so that the shear parameter g=G'/h of the central layer, G' being the shear modulus, is between $5.58 \times 10^8$ Pa/m and $2.37 \times 10^9$ Pa/m at 20° C. and for a frequency range between 100 Hz and 240 Hz, the central layer being between the two outer layers.

According to another feature, the thickness h of the central layer is such that h is between 0.50 and 0.90 mm and such that G'/h is between $7.56 \times 10^8$ Pa/m and $1.42 \times 10^9$ Pa/m at 20° C. and for a frequency range between 100 Hz and 240 Hz.

According to another feature, the central layer has a loss factor tan δ greater than 0.6.

According to another feature, the outer layers have a shear modulus G' between $10^8$ Pa and $2 \times 10^8$ Pa at 20° C. and for a frequency range between 100 Hz and 240 Hz.

According to another feature, each of the outer layers has a thickness e such that:
- the adhesion of the material of the outer layers is compatible with the requirements of Regulation R43, the adhesion being determined by twisting a specimen of interlayer constituted of the material of the outer layers bonded to two glass sheets, by measuring the torsional force for which the separation of the interlayer constituted of the material of the outer layers from the glass sheets is initiated, and by calculating, from this force, the corresponding adhesive shear strength, then by comparing this value of the adhesive strength to a range of admissible values so that any laminated glazing unit withstands the stresses corresponding to Regulation R43; and such that the thickness e of each of the outer layers is set so as to satisfy the requirements of Regulation R43, the thickness e being determined in the following manner:
- a reference laminated glazing unit is identified which withstands the stresses corresponding to Regulation R43 and which comprises two glass sheets and an interlayer constituted of the material of the outer layers;
- the tear strength of the interlayer of the reference laminated glazing unit, the thickness of the interlayer of the reference laminated glazing unit and the thickness of the glass sheets of the reference laminated glazing unit are determined;
- using a graph representative of the minimum interlayer tear strength required so that any laminated glazing unit withstands the stresses corresponding to Regulation R43, as a function of the interlayer thickness of any laminated glazing unit, this graph being established for a substrate thickness of any laminated glazing unit equal to the substrate thickness in the reference laminated glazing unit, the minimum required interlayer thickness is deduced which corresponds to a minimum required interlayer tear strength value equal to the tear strength of the interlayer of the reference laminated glazing unit; and the thickness e of each outer layer is set so that e is greater than or equal to said optimum interlayer thickness value.

According to another feature, the central layer comprises:
a damping film made of a viscoelastic plastic material A of thickness $h_A$ and with a shear parameter $g_A$;
a damping film made of a viscoelastic plastic material B of thickness $h_B$ and with a shear parameter $g_B$,
the materials A and B each having, over a respective temperature range $t_A$ and $t_B$ and for a frequency between 100 Hz and 240 Hz, a loss factor greater than 0.6 and a shear parameter between $5.58 \times 10^8$ Pa/m and $2.37 \times 10^9$ Pa/m, and the film which has the highest loss factor, for a given range of temperatures included within the temperature range $t_A$ or $t_B$ respectively, has an equivalent shear parameter $g_{A\ or\ B}$ $eq = g_{A\ or\ B} \times h$, $g_{A\ or\ B}$ being the shear parameter of the material constituting the film and h being the thickness of the central layer, which is less than the equivalent shear parameter of the other film for said temperature range.

The invention also relates to a glazing unit comprising:
a glass sheet having a thickness between 1.4 mm and 2.1 mm,
a glass sheet having a thickness between 1.1 mm and 1.6 mm, and
an interlayer described above, the interlayer being between the glass sheets.

According to another feature, the thickness e of each of the outer layers and the total thickness of the glass sheets are such that:
the adhesion of the material of the outer layers is compatible with the requirements of Regulation R43, the adhesion being determined by twisting a specimen of interlayer constituted of the material of the outer layers bonded to two glass sheets, by measuring the torsional force for which the separation of the interlayer constituted of the material of the outer layers from the glass sheets is initiated, and by calculating, from this force, the corresponding adhesive shear strength, then by comparing this value of the adhesive strength to a range of admissible values so that any laminated glazing unit withstands the stresses corresponding to Regulation R43; and such that
the thickness e of each of the outer layers and the total thickness of the glass sheets are set so as to satisfy the requirements of Regulation R43; they are determined in the following manner:
a reference laminated glazing unit is identified which withstands the stresses corresponding to Regulation R43 and which comprises two glass sheets and an interlayer constituted of the material of the outer layers;
the tear strength of the interlayer of the reference laminated glazing unit, the thickness of the interlayer of the reference laminated glazing unit and the thickness of the glass sheets of the reference laminated glazing unit are determined;
using a graph representative of the minimum interlayer tear strength required so that any laminated glazing unit withstands the stresses corresponding to Regulation R43, as a function of the interlayer thickness of any laminated glazing unit, and of the thickness of glass sheets of any laminated glazing unit, a combination of optimum values of the interlayer thickness and of the thickness of glass sheets is deduced which corresponds to a minimum required interlayer tear strength value equal to the tear strength of the interlayer of the reference laminated glazing unit; and
the thickness e of each outer layer is set so that e is greater than or equal to said optimum interlayer thickness value and the thickness of the glass sheets is set greater than or equal to said optimum glass sheet thickness value.

The invention also relates to a vehicle comprising the glazing unit as described above, the glass sheet having a thickness between 1.4 mm and 2.1 mm being turned toward the outside of the vehicle and the glass sheet having a thickness between 1.1 mm and 1.6 mm being turned toward the inside of the vehicle.

The invention also relates to the use of the interlayer as described above for the vibroacoustic damping of the second and third natural frequencies of a windshield constituted of two glass sheets and the interlayer incorporated between the glass sheets.

The invention also relates to the use of the glazing unit described above as a vehicle windshield.

As should be apparent, the invention can provide a number of advantageous features and benefits. It is to be understood that, in practicing the invention, an embodiment can be constructed to include one or more features or benefits of embodiments disclosed herein, but not others. Accordingly, it is to be understood that the preferred embodiments discussed herein are provided as examples and are not to be construed as limiting, particularly since embodiments can be formed to practice the invention that do not include each of the features of the disclosed examples.

BRIEF DESCRIPTION OF THE DRAWINGS

Other features and advantages of the invention will now be described with respect to the drawings, in which:

FIG. 2 represents a cross-sectional view of a glazing unit according to the invention;

FIG. 3 represents a cross-sectional view of a glazing unit according to the invention, according to another embodiment;

FIG. 4 represents a graph that is representative of the minimum interlayer tear strength required in order for a laminated glazing unit to withstand the stresses corresponding to Regulation R43, as a function of the interlayer thickness of the laminated glazing unit, established for a laminated glazing unit comprising two glass substrates having a thickness of 2.1 mm and an interlayer having an adhesive strength between 2 MPa and 5 MPa and for a drop height of 4 m;

FIG. 5 represents a three-dimensional graph, which is representative of the minimum interlayer tear strength required in order for a laminated glazing unit to withstand the stresses corresponding to Regulation R43, as a function both of the interlayer thickness and of the glass thickness of the laminated glazing unit, established for a laminated glazing unit comprising an interlayer having an adhesive strength between 2 MPa and 5 MPa and for a drop height of 4 m;

FIG. 6 represents a schematic front view of an experimental device for evaluating the adhesion of an interlayer with respect to glass sheets with which it is combined;

DETAILED DESCRIPTION OF THE PREFERRED EMBODIMENTS

The reference numbers which are identical on the various figures represent identical or similar components.

It should also be noted that the limits of the intervals given in this application are included in the intervals.

The invention proposes a method for selecting a viscoelastic plastic interlayer comprising two outer layers and one central layer and is intended to be incorporated between two glass sheets of a glazing unit.

The method comprises the following steps:
a first component made of a viscoelastic plastic material intended to constitute the central layer and a second component made of a viscoelastic plastic material intended to constitute the outer layers are provided,
the shear modulus G' of the first component and of the second component are measured by means of a viscoanalyzer,
the material of the second component is only selected if its shear modulus G' is greater than or equal to $3 \times 10^7$ Pa at 20° C. and for a frequency range between 100 Hz and 240 Hz; and
the thickness h of the first component is set so that h is between 0.31 mm and 1.20 mm and so that the shear parameter g=G'/h, G' being the shear modulus, is between $5.58 \times 10^8$ Pa/m and $2.37 \times 10^9$ Pa/m at 20° C. and for a frequency range between 100 Hz and 240 Hz.

The frequency range between 100 Hz and 240 Hz includes the four first natural frequencies of a laminated windshield, and in particular the second and third natural frequencies, as the inventors have been able to measure them by vehicle tests.

Furthermore, the inventors have demonstrated that the material which fulfills the conditions of h and g described above makes it possible to optimize the damping of the first natural frequencies of a laminated windshield, in particular of the second and third natural frequencies of the windshield comprising two glass sheets and an interlayer selected as described above.

Figure 1:
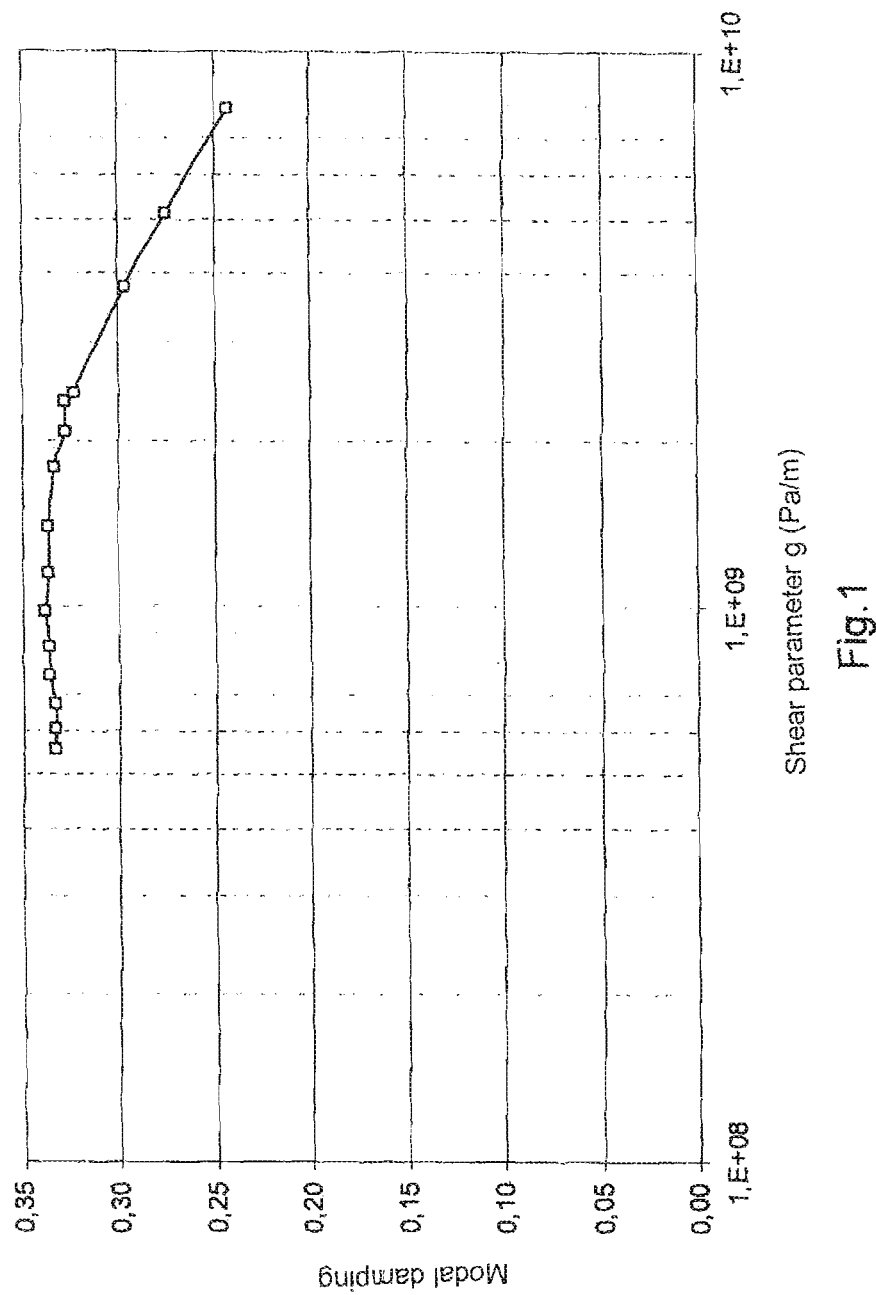
FIG. 1 represents a curve of the modal damping of a laminated windshield as a function of the shear parameter of a central layer of the interlayer of the laminated windshield for frequencies between 100 Hz and 240 Hz at 20° C., and for thicknesses of the central layer between 0.10 and 1.20 mm.

Specifically, as will be seen further on, in particular during the study of FIG. 1, the inventors have shown that these values of g between $5.58 \times 10^8$ Pa/m and $2.37 \times 10^9$ Pa/m for a frequency range between 100 Hz and 240 Hz, combined with values of h between 0.31 and 1.20 mm, make it possible to optimize the acoustic damping of frequencies between 100 Hz and 240 Hz.

If the material of the first component is such that its shear parameter g cannot be between $5.58 \times 10^8$ Pa/m and $2.37 \times 10^9$ Pa/m for a thickness between 0.31 and 1.20 mm, the material is not selected for producing the interlayer.

Furthermore, in order for the central layer to vibrate correctly, it is necessary for the outer layers to be more rigid than the central layer, which is achieved with the elasticity conditions as defined.

The invention also relates to a viscoelastic plastic interlayer intended to be incorporated between two glass sheets of a glazing unit in order to give it vibroacoustic damping properties, the interlayer comprising:
two outer layers made of a viscoelastic plastic material, the shear modulus G' of which is greater than or equal to $3 \times 10^7$ Pa at 20° C. and for a frequency range between 100 Hz and 240 Hz,
a central layer having improved vibroacoustic damping properties, of thickness h, so that h is between 0.31 mm and 1.20 mm and so that the shear parameter g=G'/h of the central layer, G' being the shear modulus, is between $5.58 \times 10^8$ Pa/m and $2.37 \times 10^9$ Pa/m at 20° C. for a frequency range between 100 Hz and 240 Hz.

The interlayer is obtained by the selection method described above.

The interlayer makes it possible to optimize the damping of the first natural frequencies of a laminated windshield, in particular of the second and third natural frequencies of the windshield, the laminated windshield comprising two glass sheets and the interlayer incorporated between the glass sheets.

The interlayer is intended to be integrated into a glazing unit. The glazing unit is intended to be used in a vehicle, in particular as a windshield.

The invention also relates to a glazing unit comprising such an interlayer. The invention also relates to a vehicle comprising such a glazing unit.

FIG. 2 represents a cross-sectional view of a glazing unit according to the invention.

The glazing unit comprises two glass sheets 1, 2 between which the interlayer is inserted. The bonding of the interlayer to the glass sheets is carried out by known means, for example by stacking the glass sheets and the interlayer and passing the assembly into an autoclave.

The glass sheet 1 of the glazing unit is intended to be turned toward the outside of the vehicle whereas the glass sheet 2 is intended to be turned toward the inside of the vehicle. The glass sheet 1 is thicker than the glass sheet 2 so that the glazing unit has a better protection against external attacks (adverse weather conditions, gravel spray, etc.). Indeed, the thicker the glass is, the better its mechanical strength. However, the thicker the glass is, the heavier it is. It is therefore necessary to find a compromise between the mechanical strength and the weight of the glazing unit. Thus, the thickness of the glass sheet 1 is, for example between 1.4 mm and 2.1 mm and the thickness of the glass sheet 2 is, for example, between 1.1 mm and 2.1 mm.

In existing glazing units, the thickness of the glass sheet 1 is, in general, 2.1 mm and the thickness of the glass sheet 2 is, in general, 1.6 mm.

Preferably, according to the invention, the thickness of the glass sheet 1 is 1.8 mm and the thickness of the glass sheet 2 is 1.4 mm in order to limit the weight of the windshield, which makes it possible to handle it more easily and to economize on material. This also makes it possible to reduce the fuel consumption of a vehicle equipped with such a windshield. These reduced thicknesses of the glass sheets are possible without loss of the acoustic or mechanical performances compared to the existing glazing units, as will be seen further on.

The invention may also apply to windshields, for which the thickness of the glass sheet 1 is 1.6 mm and the thickness of the glass sheet 2 is 1.2 mm, or else to windshields for which the thickness of the glass sheet 1 is 1.4 mm and the thickness of the glass sheet 2 is 1.1 mm.

The interlayer is constituted of two outer layers 4, 5 between which a central layer 3 is inserted.

The outer layers 4, 5 have a shear modulus G' greater than or equal to $3 \times 10^7$ Pa at 20° C. and for a frequency range between 100 Hz and 240 Hz. Preferably, the shear modulus G' of the outer layers is between $10^8$ Pa and $2 \times 10^8$ Pa in order to further improve the vibroacoustic damping of the central layer. The outer layers are, for example, made of polyvinyl butyral (PVB).

The central layer 3 is chosen so that its thickness h is between 0.31 and 1.20 mm and the shear parameter g=G'/h of the central layer, G' being the shear modulus, is between $5.58 \times 10^8$ Pa/m and $2.37 \times 10^9$ Pa/m at 20° and for a frequency range between 100 Hz and 240 Hz. The central layer 3 thus has optimized acoustic performances for the frequencies between 100 Hz and 240 Hz. The central layer is for example composed of the central layer of the three-layer acoustic PVB with the trade name SAF RZN-12 marketed by the Sekisui company or of the central layer of the three-layer acoustic PVB with trade name QC 55 marketed by Solutia Company.

In order to optimize the vibroacoustic damping even more, the central layer is preferably chosen so that h is between 0.50 mm and 0.90 mm and so that G'/h is between $7.56 \times 10^8$ Pa/m and $1.42 \times 10^9$ Pa/m at 20° C. and for a frequency range between 100 Hz and 240 Hz, which makes it possible to.

The acoustic properties of the central layer 3 are also defined by its loss factor tan δ. The central layer 3 is chosen so that its loss factor is greater than 0.6 at 20° C. and for a frequency range between 100 Hz and 240 Hz, in order to allow satisfactory damping.

The shear modulus G' and the loss factor tan δ are measured using a viscoanalyzer.

The glass sheets contribute to the vibroacoustic properties of a glazing unit. The thicker the glass sheets, the higher the excitation must be in order to make the glazing unit vibrate. However, the optimization of the acoustic performances of the interlayer for frequencies between 100 Hz and 240 Hz makes it possible to reduce the thickness of the glass sheets down to 1.8 mm, even down to 1.6 mm or even 1.4 mm, for the glass sheet intended to be turned toward the outside of the vehicle and down to 1.4 mm, even down to 1.2 mm or even 1.1 mm, for the glass sheet intended to be turned toward the inside of the vehicle, without acoustic loss relative to existing glazing units. Typically, the existing windshield glazing units have glass sheets with respective thicknesses of 2.1 mm and 1.6 mm, inserted between which is an interlayer comprising a central layer of viscoelastic plastic material having a thickness of 0.12 mm with a shear modulus G' between $5 \cdot 10^5$ and $2 \cdot 10^7$ Pa and a loss factor greater than 0.6 for a temperature of 20° C. and a frequency of 100 Hz. The reduction in the thickness of the glass sheets allows a reduction in the weight of the glazing unit, therefore improved handleability and also a reduction in material, and a reduction in the fuel consumption of a vehicle equipped with such a windshield.

The two outer layers 4, 5 have the same thickness e. The thickness e of each outer layer 4, 5 is determined both so that it is as small as possible and so that the mechanical properties of the outer layers are sufficient to satisfy the mechanical strength standards defined for motor vehicles, in particular United Nations Regulation No. 43 (referred to as Regulation R43) concerning the hard-impact strength standards. The United Nations Regulation R43 relates to the adoption of uniform technical specifications relating to the approval of safety glazing and of the installation of this glazing in road vehicles. Specifically, it is desirable for the total thickness of the interlayer to be as low as possible for reasons of weight of the windshield on the one hand, which makes it possible to reduce the fuel consumption of a vehicle equipped with such a windshield, and saving of material on the other hand.

In order to do this, the thickness e is minimized by taking into account both the adhesion of an interlayer constituted of the material of the outer layers with respect to the two glass sheets and the tear strength of the material of the outer layers.

The adhesion is evaluated on the basis of the test and calculation method described in patent application EP-A-1 495 305, which is repeated hereinbelow.

Firstly, a torsional stress is exerted on a specimen of a laminated glazing unit composed of two glass sheets and of an interlayer constituted of the material of the outer layers, until the onset of debonding of the interlayer constituted of the material of the outer layers relative to at least one of the glass sheets. In practice, the test is carried out on a round specimen 50 of glazing, having a radius r equal to 10 mm, for example using a torsion device 500 of known type, illustrated in FIG. 6.

The device 500 comprises three jaws 51, 52, 53, a pulley 54 of radius R equal to 100 mm connected to a drive chain 55 of vertical axis. The jaws are each in the form of 120° circular arcs, so as to grip the entire specimen. The surface coating of the jaws is made of a material that is mechanically compatible with the glass, for example aluminum, Teflon®, or polyethylene.

One of the jaws is held fixed against a frame, whilst another jaw is fastened to the pulley 54 that is intended to rotate in order to exert a torsion on the specimen. The pulley 54 is made to rotate by the movement of the chain 55 connected to the pulley. The chain is pulled at a minimum constant speed of 35 to 50 mm/min.

A force sensor is used to measure the force F needed to initiate the onset of debonding of the interlayer constituted of the material of the outer layers as the specimen is being twisted. From this it is then possible to deduce, by calculation, the adhesive shear strength using the known formula:

$$\tau = \frac{2FR}{\pi r^3},$$

where F is the force needed to initiate the onset of debonding of the interlayer constituted of the material of the outer layers, R is the radius of the pulley 54 and r is the radius of the specimen.

As explained in application EP-A-1 495 305, the device 500 is however bulky, which means that the tests must be carried out in the laboratory. The device 500 is therefore ill-suited to measurements of the "process indicator" type on a laminated glazing manufacturing line. However, for the manufacture of laminated glazing units, although the composition of the polymeric interlayer is designed to meet the strength values set by the invention, poor adhesion of the interlayer may nevertheless occur in the finished product due to parameters associated with the method for manufacturing the glazing unit, such as the storage conditions of the interlayer, the glass washing quality, or else the temperature and pressure forces in the course of the calendering step during assembly of the glass and the interlayer, which influence the quality of the bonding.

Figure 7:
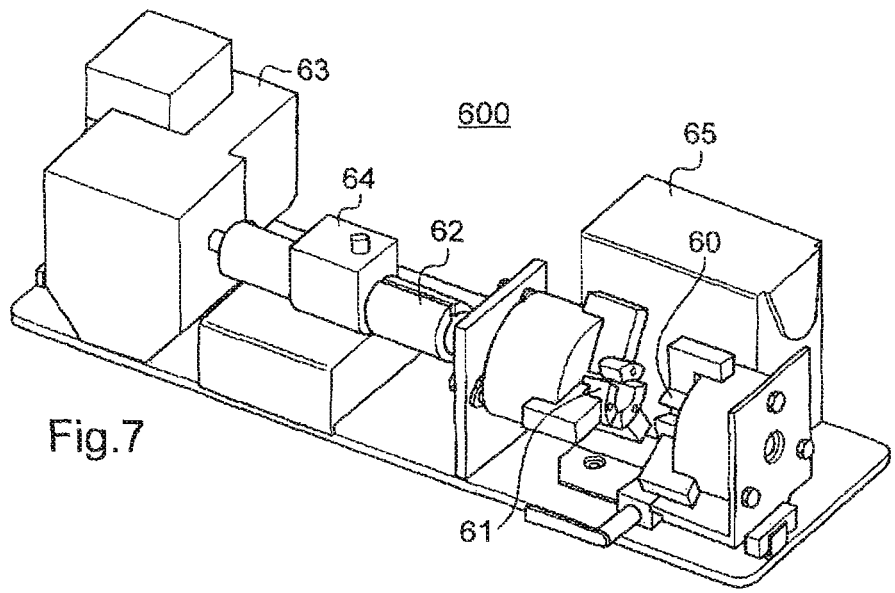
FIG. 7 represents a perspective view of a variant of a device for evaluating the adhesion of an interlayer with respect to glass sheets with which it is combined.

In order to carry out measurements during monitoring of the manufacture close to the manufacturing line so that it becomes possible to quickly intervene in the process in response to poor measured strength values, it is possible, as a variant, to use another measuring device 600 which, advantageously, is more compact and easily transportable. This device 600, represented in FIG. 7, is miniaturized to around 60 cm by 20 cm and comprises two three-jaw systems 60 and 61, a rotating shaft 62, a motor 63 for rotating the shaft, a torque meter 64 and a box 65 housing the computing elements.

The round specimen of the laminated glazing unit, composed of two glass sheets and of an interlayer constituted of the material of the outer layers, is intended to be sandwiched between the two jaw systems 60 and 61, one of the systems 60 being fixed while the other is capable of being moved and rotated by means of its connection to the shaft 62. The torque meter is placed between the motor and the moveable jaw system 61. The rotation speed of the shaft depends on the thickness of the interlayer. By way of example, for an interlayer constituted of the material of the outer layers having a thickness of 0.76 mm, the rotation is of the order of 0.08 rpm.

The system 61 rotates and when the measured torque reverses, the initiation of debonding of the interlayer constituted of the material of the outer layers has taken place. The torque meter is connected to the computing elements of the box 65, which includes a display part on which the value of the adhesive strength τ can be read directly.

Whichever device is used, with a view to having a detailed understanding of the scatter in the value of the adhesive strength τ, it is preferred to repeat the test on several specimens, for example a minimum number of five specimens, and to calculate an average of the strength τ together with its standard deviation.

It is verified that the value of the adhesive strength τ obtained is within a range of admissible values in order for any laminated glazing unit to withstand the stresses corresponding to Regulation R43 (hard-impact strength). This range of admissible values is determined experimentally, from normalized mechanical strength tests defined in Regulation R43, which were carried out on laminated glazing units of different compositions.

The range of admissible values for Regulation R43, within which any value of the adhesive strength τ is suitable for satisfying the criterion of adhesion, is all of the values below 5 MPa. Preferably, the range of admissible values of the adhesive strength τ for Regulation R43 is between 2 MPa and 5 MPa, the lower limit of this range of values being determined in order to ensure a good transparency of the glazing unit, independently of the mechanical strength considerations of the glazing unit.

Once it has been verified that the adhesive strength τ of the interlayer constituted of the material of the outer layers lies within the aforementioned range of admissible values, the actual sizing of the outer layers of the interlayer is carried out.

The graphs from FIGS. 4 and 5 illustrate two possible approaches for sizing these outer layers so that they satisfy the requirements of Regulation R43 for hard-impact strength.

According to a first approach, which corresponds to FIG. 4, a glazing unit is sized with a total thickness $e_{g\text{-}dim}$ of glass sheets in the laminated glazing unit that is fixed and equal to 4.2 mm, which corresponds, for example, to a thickness of each glass sheet of 2.1 mm, and an interlayer constituted of the material of the outer layers, of specific composition $c_i$, for example a PVB-based interlayer. The central layer is ignored for the determination of the thickness of the outer layers.

In this case, with a view to sizing the interlayer constituted of the material of the outer layers, firstly a curve $C_3$, seen in FIG. 4 and representative of the minimum interlayer tear strength $J_{c\text{-}min}$ required for any laminated glazing unit to withstand the stresses corresponding to Regulation R43, is plotted as a function of the interlayer thickness $e_i$ of any laminated glazing unit, this curve being established for a glass sheet thickness $e_g$ equal to 4.2 mm. In practice, the curve $C_3$ is obtained from normalized tests of mechanical strength defined in Regulation R43, carried out on laminated glazing units of different compositions in terms of thickness of their interlayer.

Next, a reference laminated glazing unit is identified which withstands the stresses corresponding to Regulation R43, with a glass substrate thickness equal to 4.2 mm and which comprises an interlayer having the specific composition $c_i$. An example of such a reference laminated glazing unit is the known glazing unit 2.1/0.76/2.1, which comprises two glass substrates each having a thickness of 2.1 mm and two interlayer layers having a standard thickness of 0.38 mm and having the composition $c_i$, which corresponds to an interlayer thickness $e_{i\text{-}ref}$ of the reference laminated glazing unit equal to 0.76 mm. The resistance of this reference glazing unit to the stresses corresponding to Regulation R43 is verified by a normalized mechanical strength test, in this example with an impact drop height of 4 m.

The tear strength $J_{c\text{-}ref}$ of the interlayer of the reference glazing unit 2.1/0.76/2.1 is then determined by the Tielking method.

This method, developed by M. Tielking, consists in evaluating the tear strength of a material based on a method of calculating the crack root energy J. The Tielking method is explained in particular in patent applications EP-A-1 151 855 and EP-A-1 495 305, repeated, in part, below.

The tear strength of an interlayer is a characteristic intrinsic to the material constituting it. It is characterized by an energy value representative of the energy needed to propagate a crack initiated in the material. This energy, known as the critical energy $J_c$, is different for each type of material and is independent of the thickness of the interlayer film.

The tear strength or critical energy $J_c$ is given in a known manner by an energy method based on the Rice integral J, which defines the energy localized at the root of a crack in a film subjected to very high stresses at the location of a crack. It is written in the simplified mathematical form:

$$J = -\frac{1}{e_1}\left(\frac{\partial U}{\partial a}\right),$$

for a given stretch d of the specimen tested which will hereafter be called the displacement d, and in which:
 $e_1$ is the thickness of the specimen;
 a is the length of the crack; and
 U is the potential energy of the specimen.

Figure 8:
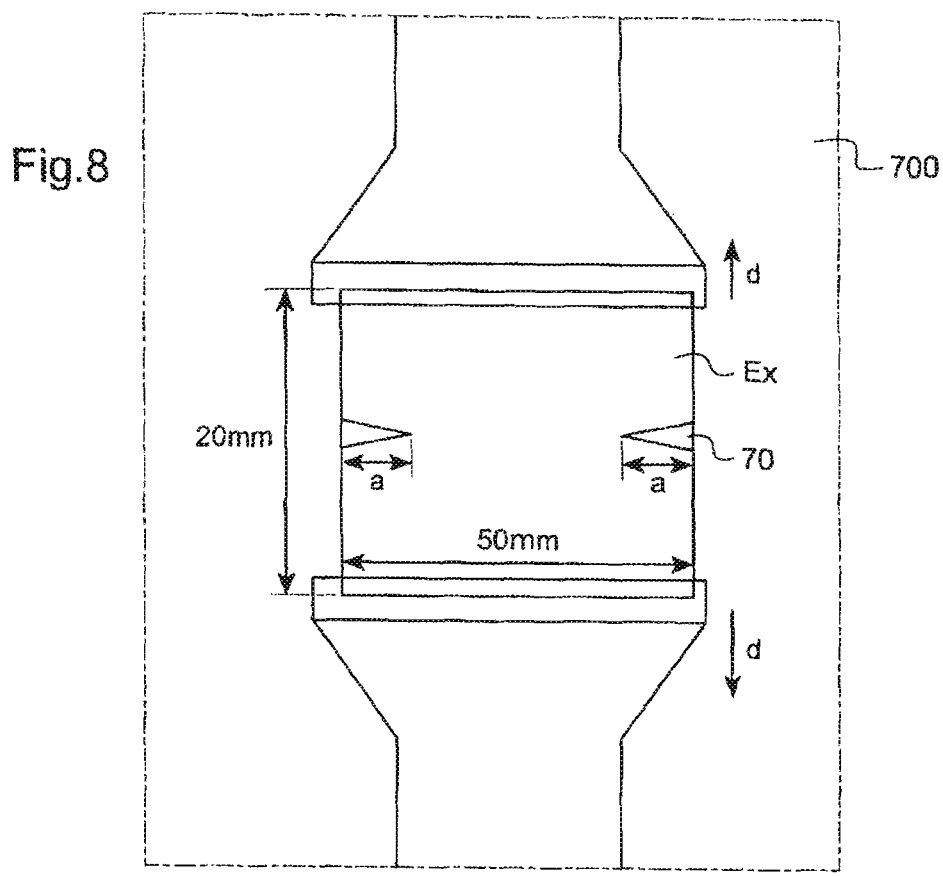
FIG. 8 represents a schematic view of an experimental device for evaluating the tear strength of an interlayer.

The experimental device for determining the tear strength is illustrated in FIG. 8. Tensile tests using a tension-compression machine 700 are carried out on several specimens $Ex_n$, for example four specimens, of the same material and with a surface area equal to 100 mm$^2$ (50 mm in length by 20 mm in width). Each specimen is notched on its sides and perpendicular to the tensile force, having a different crack length a for each specimen $Ex_n$, corresponding to 5, 8, 12 and 15 mm respectively.

Each specimen $Ex_n$ is stretched perpendicular to the cracks 20 at a stretch rate of 100 mm/min and over a given stretch length or distance d and in an environment in which the temperature is 20° C.

According to the method described in detail in EP-A-1 495 305, it is possible to establish a curve of variation of the crack root energy J as a function of the stretch d undergone by the specimen (not represented). Using a video camera which displays the propagation of the crack 70, it is then detected at which displacement $d_c$ the propagation of the crack in the specimen starts. Then, from the curve J(d☐ the value of the critical energy $J_c$ for initialization of the tearing of the specimen, corresponding to the displacement $d_c$, is deduced. It is at this critical value $J_c$ that the material tears and that it is consequently mechanically damaged with respect to the required mechanical function.

The value of the tear strength $J_{c-ref}$ measured for the interlayer of composition $c_i$ of the reference glazing unit 2.1/0.76/2.1 is 31 000 J/m².

Using the curve $C_3$ from FIG. 4, the minimum required interlayer thickness $e_{i-min}$ corresponding to a minimum required interlayer tear strength value $J_{c-min}$ equal to the tear strength of the interlayer of the reference laminated glazing unit $J_{c-ref}$ is then deduced. As shown on curve $C_3$, the minimum required interlayer thickness $e_{i-min}$ is equal to 0.45 mm.

Thus, it is possible to size the laminated glazing unit constituted of two glass sheets having a thickness of 2.1 mm each and an interlayer constituted of the material of the outer layers with a thickness $e_{i-dim}$ of the interlayer greater than or equal to the minimum required interlayer thickness $e_{i-min}$=0.45 mm. Preferably, the interlayer thickness $e_{i-dim}$ of the laminated glazing unit is greater than the minimum required interlayer thickness value $e_{i-min}$ only within a limit of 20% above this value, that is to say, in the preceding example, $e_{i-dim}$ is preferably such that 0.45 mm≤$e_{i-dim}$≤0.55 mm.

Thus a laminated glazing unit is obtained that satisfies the requirements of Regulation R43, which comprises two glass sheets 1, 2 having a thickness of 2.1 mm and an interlayer with a central layer 3 and two outer layers 4, 5, each of the outer layers having a thickness between 0.225 mm and 0.275 mm.

The curve $C_3$ can be plotted for other glass sheet values, for example 1.8 mm and 1.4 mm. Each of the outer layers then has a thickness between 0.2 mm and 0.37 mm.

According to a second possible approach for sizing the outer layers of the interlayer, which corresponds to FIG. 5, a laminated glazing unit is sized without arbitrarily setting the thickness of the glass sheets, the glazing unit comprising an interlayer constituted of the material of the outer layers.

A three-dimensional graph $C_4$ is plotted, seen in FIG. 5, that is representative of the minimum interlayer tear strength $J_{c-min}$ required in order for any laminated glazing unit to withstand the stresses corresponding to Regulation R43, as a function both of the thickness $e_i$ of the interlayer constituted of the material of the outer layers of any laminated glazing unit and of the thickness $e_g$ of the glass sheets of any laminated glazing unit. The graph $C_4$ from FIG. 5 is obtained from normalized mechanical strength tests defined in Regulation R43, carried out on laminated glazing units having different compositions in terms of interlayer thickness and of substrate thickness.

The tear strength $J_{c-ref}$ of a reference laminated glazing unit, which withstands the stresses corresponding to Regulation R43 and which comprises an interlayer having the specific composition $c_i$, is then determined.

The known laminated glazing unit 2.1/0.76/2.1 described above may, for example, act as the reference laminated glazing unit, as can the laminated glazing unit 2.1/0.76/1.8 which is also known, which comprises two glass sheets having respective thicknesses of 2.1 mm and 1.8 mm and two layers of interlayer constituted of the material of the outer layers of standard thickness 0.38 mm having the composition $c_i$, which corresponds to an interlayer thickness $e_{i-ref}$ equal to 0.76 mm. The tear strength $J_{c-ref}$ of one or the other reference glazing unit under stresses corresponding to Regulation R43 is evaluated as before by the Tielking method.

Using the graph $C_4$, a combination of optimum values $e_{i-opt}$, $e_{g-opt}$ of the thickness of the interlayer constituted of the material of the outer layers and of the thickness of glass sheets which corresponds to a minimum required interlayer tear strength value $J_{c-min}$ equal to the tear strength of the interlayer of the reference laminated glazing unit $J_{c-ref}$ is then deduced. For example, when starting from the reference glazing 2.1/0.76/2.1, which corresponds to a value of the tear strength $J_{c-ref}$ of 31 000 J/m², the points that provide a combination of optimum values $e_{i-opt}$, $e_{g-opt}$ are the points of the area, or surface, of the graph $C_4$ which correspond to a $J_{c-min}$ value of 31 000 J/m². On this subject, it is noted that each of the optimum values $e_{i-opt}$ or $e_{g-opt}$ is not necessarily, individually, a minimum value of the thickness of the interlayer constituted of the material of the outer layers or a minimum value of the thickness of the glass sheets. It is the combination of the values $e_{i-opt}$ and $e_{g-opt}$ which results in a minimized value of the overall thickness of the laminated glazing unit.

As is seen in the graph $C_4$, the combination of values $e_i$=0.5 mm and $e_g$=1.8 mm/1.4 mm is a combination of values greater than or equal to a combination of optimum values.

Hence, it is possible to size the laminated glazing unit with a thickness $e_{e-dim}$ of the interlayer constituted of the material of the outer layers that is greater than or equal to 0.5 mm and thicknesses $e_{g-dim}$ of the glass sheets of 1.8 mm and 1.4 mm, respectively, this laminated glazing unit satisfying the requirements of Regulation R43.

The interlayer of composition $c_i$ considered in the above examples has average performances from the point of view of its tear strength and the tear strength levels of compositions of better-performing interlayers currently known make it possible to envisage combinations of optimum values $e_{i-opt}$, $e_{g-opt}$ that are further reduced compared to the values given previously.

In particular, for a laminated glazing unit suitable for withstanding the stresses corresponding to Regulation R43 and that comprises two glass substrates having respective thicknesses of 1.8 mm and 1.4 mm, the minimum required interlayer thickness $e_{i-min}$ may drop to around 0.4 mm. Hence, the optimized interlayer thickness $e_{i-dim}$ of a laminated glazing unit corresponding to the requirements of Regulation R43 and that comprises two glass substrates having respective thicknesses of 1.8 mm and 1.4 mm is, generally, such that 0.4 mm 0.74 mm, the lower limit of this interval corresponding to the interlayer compositions that have high performances from the point of view of their tear strength.

Thus, a laminated glazing unit is obtained that satisfies the requirements of Regulation R43 and which comprises two glass sheets 1, 2 having respective thicknesses of 1.8 mm and 1.4 mm and an interlayer with a central layer 3 and two outer layers 4, 5, each of the outer layers having a thickness between 0.2 mm and 0.37 mm.

Thus, the thickness e of each outer layer 4, 5 is set so that they provide sufficient mechanical properties to the glazing unit, namely mechanical properties that satisfy Regulation R43. This is carried out in the following manner:

it is verified that the adhesion of the material of the outer layers is compatible with the requirements of Regulation R43 by twisting a specimen of the interlayer constituted of the material of the outer layers bonded to two glass sheets, by measuring the torsional force (F) at which separation of the interlayer constituted of the material of the outer layers from the glass sheets is initiated, and by calculating from this force (F) the corresponding adhesive shear strength ($\tau$), and this value of the adhesive strength ($\tau$) is compared with a range of admissible values so that any laminated glazing unit withstands the stresses corresponding to Regulation R43; and the thickness e of each of the outer layers so that they satisfy the requirements of Regulation R43 is set in the following manner:

a reference laminated glazing unit is identified that withstands the stresses corresponding to Regulation R43 and which comprises two sheets of glass and an interlayer constituted of the material of the outer layers;

the tear strength ($J_{c\text{-}ref}$) of the interlayer of the reference laminated glazing unit, the thickness ($e_{i\text{-}ref}$) of the interlayer of the reference laminated glazing unit and the thickness ($e_{g\text{-}ref}$) of the glass sheets of the reference laminated glazing unit are determined;

using a graph ($C_3$) representative of the minimum interlayer tear strength ($J_{c\text{-}min}$) required so that any laminated glazing unit withstands the stresses corresponding to Regulation R43, as a function of the interlayer thickness ($e_i$) of any laminated glazing unit, this graph being established for a substrate thickness of any laminated glazing unit equal to the substrate thickness in the reference laminated glazing unit ($e_g = e_{g\text{-}ref}$), the minimum required interlayer thickness ($e_{i\text{-}min}$) is deduced which corresponds to a minimum required interlayer tear strength value equal to the tear strength of the interlayer of the reference laminated glazing unit ($J_{c\text{-}min} = J_{c\text{-}ref}$); and the thickness e of each outer layer is set so that e is greater than or equal to said optimum interlayer thickness value ($e_{i\text{-}opt}$).

As a variant, both the thickness e of each outer layer 4, 5 and the thickness of the glass sheets are set so that the assembly provides sufficient mechanical properties to the glazing unit, namely mechanical properties that satisfy Regulation R43. This is carried out in the following manner:

it is verified that the adhesion of the material of the outer layers is compatible with the requirements of Regulation R43 by twisting a specimen of the interlayer constituted of the material of the outer layers bonded to two glass sheets, by measuring the torsional force (F) at which separation of the interlayer constituted of the material of the outer layers from the glass sheets is initiated, and by calculating from this force (F) the corresponding adhesive shear strength ($\tau$), and this value of the adhesive strength ($\tau$) is compared with a range of admissible values so that any laminated glazing unit withstands the stresses corresponding to Regulation R43; and the thickness e of each of the outer layers and the total thickness of the glass sheets so that they satisfy the requirements of Regulation R43 is set in the following manner:

a reference laminated glazing unit is identified that withstands the stresses corresponding to Regulation R43 and which comprises two sheets of glass and an interlayer constituted of the material of the outer layers;

the tear strength ($J_{c\text{-}ref}$) of the interlayer of the reference laminated glazing unit, the thickness ($2e_{\text{-}ref}$) of the interlayer of the reference laminated glazing unit and the thickness ($e_{g\text{-}ref}$) of the glass sheets of the reference laminated glazing unit are determined;

using a graph ($C_4$) representative of the minimum interlayer tear strength ($J_{c\text{-}min}$) required so that any laminated glazing unit withstands the stresses corresponding to Regulation R43, as a function of the interlayer thickness ($e_i$) of any laminated glazing unit, and of the thickness of glass sheets ($e_g$) of any laminated glazing unit, a combination of optimum values ($e_{i\text{-}opt}$, $e_{g\text{-}opt}$) of the interlayer thickness and of the thickness of glass sheets is deduced which corresponds to a minimum required interlayer tear strength value equal to the tear strength of the interlayer of the reference laminated glazing unit ($J_{c\text{-}min} = J_{c\text{-}ref}$); and the thickness e of each outer layer is set so that e is greater than or equal to said optimum interlayer thickness value ($e_{i\text{-}opt}$) and the thickness of the glass sheets ($e_{g\text{-}dim}$) is set greater than or equal to said optimum glass sheet thickness value ($e_{g\text{-}opt}$).

The total thickness of the interlayer is preferably less than or equal to 0.86 mm.

FIG. 3 represents a cross-sectional view of a glazing unit according to the invention, according to another embodiment.

The glass sheets 1, 2 and the outer layers 4, 5 of the interlayer are identical with respect to those from FIG. 2.

The central layer 3 comprises two damping films 6, 7. The damping film 6 is constituted of a viscoelastic plastic material A, which is different from the viscoelastic material B of which the damping film 7 is constituted. According to one embodiment, the materials A, B are coextruded. As a variant, they are laminated.

The damping films 6, 7 constituting the central layer 3 make it possible to optimize the damping of the acoustic vibrations over different temperature ranges. Thus, the film 6 optimally damps acoustic vibrations over a first temperature range and the film 7 optimally damps acoustic vibrations over a second temperature range. The first and second temperature ranges do not overlap. This makes it possible to optimize the damping of frequencies between 100 Hz and 240 Hz over a wider temperature range.

In order to do this, the material A is chosen to have, over a temperature range $t_A$ and for a frequency between 100 Hz and 240 Hz, a loss factor greater than 0.6 and a shear parameter between $5.58 \times 10^8$ Pa/m and $2.37 \times 10^9$ Pa/m. Likewise, the material B is chosen to have, over a temperature range $t_B$ and for a frequency between 100 Hz and 240 Hz, a loss factor greater than 0.6 and a shear parameter between $5.58 \times 10^8$ Pa/m and $2.37 \times 10^9$ Pa/m.

Furthermore, the film 6 or 7 which has the highest loss factor for a given temperature range included within the temperature range respectively $t_A$ or $t_B$, has an equivalent shear parameter $g_{AorB\ eq} = h \times g_{AorB}$, $g_{AorB}$ being the shear parameter of the material respectively A or B respectively constituting the film 6 or 7 and h being the thickness of the central layer, which is much lower than the equivalent shear parameter of the other film 7 or 6 respectively for said given temperature range. The equivalent shear parameter corresponds to the shear modulus.

The given temperature range is the first temperature or the second temperature range in which the film 6 or 7 respectively optimally damps the acoustic vibrations at frequencies between 100 Hz and 240 Hz.

Thus, it is not only necessary for the loss factor of each of the films 6, 7 to be greater than 0.6 and for the shear parameter of the material of each of the films to be between $5.58 \times 10^8$ Pa/m and $2.37 \times 10^9$ Pa/m within its corresponding temperature range, but it is necessary for the most damping film (highest tan δ) in the corresponding temperature range to have an equivalent shear modulus that is much lower than the other film. In this way, the interlayer will have a behavior similar to the most damped film over each temperature range. The interlayer will thus provide optimum damping over each of the temperature ranges for which each of the films constituting the interlayer plays an optimum damping role.

Proof will now be provided that the damping of the frequencies between 100 Hz and 240 Hz is indeed optimal for the ranges of g described above.

FIG. 1 represents a curve of the modal damping of a laminated windshield as a function of the shear parameter of a central layer of the interlayer of the laminated windshield for frequencies between 100 Hz and 240 Hz at 20° C. This curve has been calculated by a finite element method.

The calculation was carried out for a windshield constituted of two glass sheets having respective thicknesses of 1.4 mm and 1.8 mm, between which an interlayer made of a viscoelastic plastic material is incorporated. The interlayer comprises three layers: a central layer incorporated between two outer layers. Each point of the curve from FIG. 1 represents the value for modal damping as a function of shear parameter for a thickness h of the central layer, the various points corresponding to thicknesses h between 0.10 mm and 1.20 mm.

Table 1 below covers values for the shear parameter g and values for the modal damping for each value of h.

TABLE 1

| H (mm) | G (Pa/m) | Modal damping |
|---|---|---|
| 0.10 | $7.958 \times 10^9$ | 0.2421 |
| 0.15 | $5.164 \times 10^9$ | 0.2737 |
| 0.20 | $3.793 \times 10^9$ | 0.2959 |
| 0.30 | $2.449 \times 10^9$ | 0.3235 |
| 0.31 | $2.366 \times 10^9$ | 0.3273 |
| 0.35 | $2.076 \times 10^9$ | 0.3273 |
| 0.40 | $1.796 \times 10^9$ | 0.3327 |
| 0.50 | $1.414 \times 10^9$ | 0.3365 |
| 0.60 | $1.163 \times 10^9$ | 0.3365 |
| 0.70 | $9.864 \times 10^8$ | 0.3381 |
| 0.80 | $8.570 \times 10^8$ | 0.3365 |
| 0.90 | $7.564 \times 10^8$ | 0.3365 |
| 1.00 | $6.759 \times 10^8$ | 0.3327 |
| 1.10 | $6.112 \times 10^8$ | 0.3327 |
| 1.20 | $5.583 \times 10^8$ | 0.3327 |

As is shown in FIG. 1 and Table 1, the range of the shear parameter g between $5.58 \times 10^8$ Pa/m and $2.37 \times 10^9$ Pa/m for a central layer 3 having a thickness h between 0.31 mm and 1.20 mm, at 20° C. and for a frequency range between 100 Hz and 240 Hz, enables a modal damping greater than or equal to 0.327, which is therefore very good since the maximum of the curve is at 0.338 for a central layer thickness of 0.7 mm.

The range of the shear parameter g between $7.56 \times 10^8$ Pa/m and $1.42 \times 10^9$ Pa/m for a central layer 3 having a thickness h between 0.50 mm and 0.90 mm, at 20° C. and for a frequency range between 100 Hz and 240 Hz, enables a modal damping greater than or equal to 0.336, which is therefore an optimized damping.

Therefore, the invention does indeed make it possible to optimize the vibroacoustic damping of the first natural frequencies of a windshield comprising the interlayer as described above.

The interlayer according to the invention also enables good vibroacoustic damping outside of the frequency range for which it is optimized.

The insert according to the invention is preferably used, between two glass sheets, for a windshield. It may also be used in a side glazing or in glazing for the roof of a vehicle, for example of an automobile vehicle.

Obviously, numerous modifications and variations of the present invention are possible in light of the above teachings. It is therefore to be understood that within the scope of the appended claims, the invention may be practiced otherwise than as specifically described therein.

What is claimed:

1. A method for selecting a viscoelastic plastic interlayer including two outer layers and a central layer configured to be incorporated between two sheets of glass of a glazing unit, the method comprising:
   providing a first component made of a viscoelastic plastic material intended to constitute the central layer and a second component made of a viscoelastic plastic material intended to constitute the two outer layers, the central layer being located between the two outer layers,
   measuring the shear modulus G' of the first component and of the second component by a viscoanalyzer;
   selecting the material of the second component only if its shear modulus G' is greater than or equal to $3 \times 10^7$ Pa at 20° C. and for a frequency range between 100 Hz and 240 Hz; and
   setting the thickness h of the first component so that h is between 0.50 mm and 0.90 mm and so that the shear parameter g=G'/h, G' being the shear modulus, is between $7.56 \times 10^8$ Pa/m and $1.42 \times 10^9$ Pa/m at 20° C. and for a frequency range between 100 Hz and 240 Hz,
   wherein the interlayer is an acoustic polyvinyl butyral (PVB) that includes at least the two outer layers and the central layer.

2. The method as claimed in claim 1, further comprising:
   before the step of setting the thickness h, measuring the loss factor tan δ of the first component by means of the viscoanalyzer; and
   selecting the first component only if its loss factor tan δ is greater than 0.6.

3. The method as claimed in claim 1, further comprising:
   selecting the material of the second component only if its shear modulus G' is between $10^8$ Pa and $2 \times 10^8$ Pa at 20° C. and for a frequency range between 100 Hz and 240 Hz.

4. The method as claimed in claim 1, further comprising:
   verifying that the adhesion of the material of the second component is compatible with the requirements of Regulation R43 by twisting a specimen of the interlayer constituted of the material of the second component bonded to two glass sheets, by measuring the torsional force (F) at which separation of the interlayer constituted of the material of the second component from the glass sheets is initiated, and by calculating from this force (F) the corresponding adhesive shear strength ($\tau$), and this value of the adhesive strength ($\tau$) is compared with a range of admissible values so that any laminated glazing unit withstands the stresses corresponding to Regulation R43; and setting the thickness e of the second component in the following manner:

identifying a reference laminated glazing unit that withstands the stresses corresponding to Regulation R43 and which includes two sheets of glass and an interlayer constituted of the material of the second component;

determining the tear strength (Jc-ref) of the interlayer of the reference laminated glazing unit, the thickness (ei-ref) of the interlayer of the reference laminated glazing unit and the thickness (eg-ref) of the glass sheets of the reference laminated glazing unit;

using a graph (C3) representative of the minimum interlayer tear strength (Jc-min) required so that any laminated glazing unit withstands the stresses corresponding to Regulation R43, as a function of the interlayer thickness (ei) of any laminated glazing unit, this graph being established for a substrate thickness of any laminated glazing unit equal to the substrate thickness in the reference laminated glazing unit (eg=eg-ref), the minimum required interlayer thickness (ei-min) is deduced which corresponds to a minimum required interlayer tear strength value equal to the tear strength of the interlayer of the reference laminated glazing unit (Jc-min=Jc-ref); and setting the thickness e of the second component so that e corresponds to an interlayer thickness value greater than or equal to said minimum required interlayer thickness (ei-min) as an optimum interlayer thickness value (ei-opt).

* * * * *